(12) United States Patent
Innis et al.

(10) Patent No.: US 6,677,445 B1
(45) Date of Patent: Jan. 13, 2004

(54) CHIMERIC ANTISENSE OLIGONUCLEOTIDES AND CELL TRANSFECTING FORMULATIONS THEREOF

(75) Inventors: Michael A. Innis, Moraga, CA (US); Christoph J. Reinhard, Alameda, CA (US); Ronald N. Zuckermann, El Cerrito, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/648,254

(22) Filed: Aug. 25, 2000

Related U.S. Application Data

(60) Provisional application No. 60/151,246, filed on Aug. 27, 1999.

(51) Int. Cl.$^7$ ............................................... C07H 21/04
(52) U.S. Cl. ................... 536/24.5; 536/23.1; 536/24.31; 536/24.33
(58) Field of Search .................. 435/6, 91.1; 536/23.1, 536/24.1, 24.31, 24.33, 24.5; 436/71

(56) References Cited

U.S. PATENT DOCUMENTS

| | | |
|---|---|---|
| 4,904,582 A | 2/1990 | Tullis |
| 5,246,921 A | 9/1993 | Reddy et al. |
| 5,272,065 A | 12/1993 | Inouye et al. |
| 5,366,878 A | 11/1994 | Pederson et al. |
| 5,563,255 A | 10/1996 | Monia et al. |
| 5,576,208 A | 11/1996 | Monia et al. |
| 5,583,032 A | 12/1996 | Torrence et al. |
| 5,614,503 A | 3/1997 | Chaudhary et al. |
| 5,624,824 A | 4/1997 | Yuan et al. |
| 5,627,274 A | 5/1997 | Kole et al. |
| 5,635,377 A | 6/1997 | Pederson et al. |
| 5,652,355 A | 7/1997 | Smith |
| 5,652,356 A | 7/1997 | Agrawal |
| 5,656,462 A | 8/1997 | Keller et al. |
| 5,663,153 A | 9/1997 | Hutcherson et al. |
| 5,677,289 A | 10/1997 | Torrence et al. |
| 5,686,242 A | 11/1997 | Bruice et al. |
| 5,700,922 A | 12/1997 | Cook |
| 5,719,131 A | 2/1998 | Harris et al. |
| 5,726,059 A | 3/1998 | Wickens et al. |
| 5,731,146 A | 3/1998 | Duck et al. |
| 5,744,308 A | 4/1998 | Guillou-Bonnici et al. |
| 5,744,362 A | 4/1998 | Monia et al. |
| 5,773,601 A | 6/1998 | Agrawal |
| 5,801,154 A * | 9/1998 | Baracchini et al. |
| 5,814,500 A | 9/1998 | Dietz |
| 5,824,517 A | 10/1998 | Cleuziat et al. |
| 5,849,902 A | 12/1998 | Arrow et al. |
| 5,853,990 A | 12/1998 | Winger et al. |
| 5,856,455 A | 1/1999 | Cook |
| 5,877,162 A | 3/1999 | Werner et al. |
| 5,886,165 A | 3/1999 | Kandimalla et al. |
| 5,891,714 A | 4/1999 | Ashley et al. |
| 5,898,031 A | 4/1999 | Crooke |
| 5,916,808 A | 6/1999 | Kole et al. |
| 5,935,936 A * | 8/1999 | Fasbender et al. |
| 5,935,937 A | 8/1999 | Smith |
| 5,958,773 A | 9/1999 | Monia et al. |
| 6,197,332 B1 * | 3/2001 | Zuckermann et al. |

FOREIGN PATENT DOCUMENTS

| | | |
|---|---|---|
| DE | 197 50 702 A1 | 5/1999 |
| WO | WO 98/06437 | 1/1998 |
| WO | WO 98/13536 | 4/1998 |
| WO | WO 98/49348 | 11/1998 |
| WO | WO 99/08711 | 2/1999 |
| WO | WO 99/25819 | 5/1999 |

OTHER PUBLICATIONS

D.D.F. Ma et al., Synthetic oligonucleotides as therapeutics: the coming of age, Biotechnology Annual Review, vol. 5, pp. 155–196, 2000.*

Chin–Yi Huang et al., Liptoids—novel cationic lipids for cellular delivery of plasmid DNA in vitro, Chemistry & Biology, 1998, vol. 5, No. 6, pp. 345–354.*

Ekambar R. Kandimalla et al., Synthesis and properties of 2'– O – Methylribonucleotide methylphosphonate containing chimeric oligonucleotides, Nucleosides & Nucleotides, 14(3–5), pp. 1031–1035, 1995.*

Angus I. Lamond et al., Antisense oligonucleotides made of 2'– O– alkyl1RNA: their properties and applications in RNA biochemistry, FEBS 12462, vol. 325, No. 1, 2, Jun. 1993, pp. 123–127.*

Agrawal, "Antisense Oligonucleotides: Towards Clinical Trials" *TIBTECH* vol. 14, Oct., 1996.

Agrawal et al., "Site–Specific Excision from RNA by RNase H and Mixed–Phosphate–Backbone Oligodeoxynucleotides" *Proc. Natl. Acad. Sci. USA* 87:1401–1405, Feb., 1990.

(List continued on next page.)

*Primary Examiner*—John L. LeGuyader
*Assistant Examiner*—M Schmidt
(74) *Attorney, Agent, or Firm*—LeeAnn Gorthey; Steven W. Collier; Robert P. Blackburn

(57) ABSTRACT

Chimeric oligonucleotide of the formula 5'-W-X$^1$-Y-X$^2$-Z-3', where W represents a 5'-O-alkyl nucleotide, each of X$^1$ and X$^2$ represents a block of seven to twelve phosphodiester-linked 2'-O-alkyl ribonucleotides, Y represents a block of five to twelve phosphorothioate-linked deoxyribonucleotides, and Z represents a blocking group effective to block nuclease activity at the 3' end of the oligonucleotide, are described. These compounds exhibit high resistance to endo- and exonucleases, high sequence specificity, and the ability to activate RNAse H, as evidenced by efficient and long-lasting suppression of target mRNA. The oligonucleotides are preferably transfected into cells in formulations containing a lipid-peptoid conjugate carrier molecule of the formula L-linker-[N(CH$_2$CH$_2$NH$_2$)CH$_2$(C=O)—
    N(CH$_2$CH$_2$R)CH$_2$(C=O)—N(CH$_2$CH$_2$R)CH$_2$(C=O)]$_3$—NH$_2$, where L is a lipid moiety, including a steroid, and each group R is independently selected from alkyl, aminoalkyl, and aralkyl.

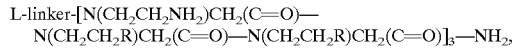

7 Claims, 13 Drawing Sheets

OTHER PUBLICATIONS

Agrawal et al., "Mixed–Backbone Oligonucleotides as Second Generation Antisense Oliognucleotides: In vitro and In vivo Studies" *Proc. Natl. Acad. Sci. USA* 94:2620–2625, Mar., 1997.

Altmann et al., Chapter 4, entitled "Novel Chemistry" Applied Antisense Oligonucleotide Technology, edited by Stein and Krieg, 1998, pp. 73–107.

Atabekov et al., "Site–Specific Enzymatic Cleavage of TMV RNA directed by Deoxyribo– and Chimeric (deoxyribo–ribo) Oligonucleotides" *FEB* 232:96–98, May., 1998.

Baertschi, "Antisense Oligonucleotide Strategies in Physiology" *Molecular and Cellular Endocrinology* 101:R15–R25, 1994.

Bhan et al., "2', 5'–Linked Oligo–3'–Deoxyribonucleoside Phosphorothioate Chimeras: Thermal Stability and Antisense Inhibition of Gene Expression" *Nucleic Acids Research* 25(16):3310–3317, 1987.

Cook, Chapter 9, entitled "Medicinal Chemistry Strategies for Antisense Research" CRC Press, Inc., 1993.

Crooke, "Progress in Antisense Therapeutics" *Hematologic Pathology* 9(2):59–72, 1995.

Cruse et al., "Chiral Phosphorothioate Analogues of B–DNA" *J. Mol. Biol.* 192:891–905, 1986.

Damha et al., "Antisense L/D–Oligodeoxynucleotide Chimeras: Nuclease Stability, Base–Pairing Properties, and Activity at Directing Ribonuclease H" *Biochemistry* 33:7877–7885, 1994.

Eckstein et al., "Nucleoside Phosphorothioates" *J. American Chemistry Society* 92(15):4718–4723, Jul. 29, 1970.

Fujii et al., "Acylphosphonates" *Tetrahedron* 43(15):3395–3407, 1987.

Furdon et al., "RNase H Cleavage of RNA Hybridized to Oligonucleotides Containing Methylphosphonate, Phosphorothioate and Phosphodiester Bonds" *Nucleic Acids Research* 17(22):9193–9204, 1989.

Gao et al., "Phosphorothioate Oligonucleotides are Inhibitors of Human DNA Polymerases and RNase H: Implications for Antisense Technology" *Molecular Pharmacology* 41:223–229, Feb. 1992.

Goodchild, "Conjugates of Oligonucleotides and Modified Oligonucleotides: A Review of Their Synthesis and Properties" *Bioconjugate Chemistry* 1(3):165–187, May/Jun., 1990.

Gee et al., "Assessment of High–Affinity Hybridization, RNase H Cleavage, and Covalent Linkage in Translation Arrest by Antisense Oligonucleotides" *Antisense and Nucleic Acids Drug Development* 8:103–111, 1998.

Godard et al., "Antisense Effects of Cholesterol–Oligodeoxynucleotide Conjugates Associated with Poly(alkylcyanoarylate) Nanoparticles" *Eur. J. Biochem.* 232:404–410, 1995.

Gottikh et al., "Alpha Beta Chimeric Antisense Oligonucleotides: Synthesis and Nuclease Resistance in Biological Media" *Antisense Research and Development* 4:251–258, 1994.

Hoke et al., "Effects of Phosphorothioate Capping on Antisense Oligonucleotide Stability, Hybridization and Antiviral Efficacy Versus Herpes Simplex Virus Infection" *Nucleic Acids Research* 19(20):5743–5748, 1991.

Inoue et al., "Sequence–Specific Cleavage of RNA Using Chimeric DNA Splints and RNase H" *Nucleic Acids Research* Symposium Series No. 19, pp. 135–138, 1988.

Inoue et al., "Sequence–Dependent Hydrolysis of RNA Using Modified Oligonucleotide Splints and RNase H" *Nucleic Acids Research* Symposium Series, No. 18, 1987, pp. 221–224.

Inoue et al., "Sequence–Dependent Hydrolysis of RNA Using Modified Oligonucleotide Splints and RNase H" *FEB* 215(2):327–330, May, 1987.

Kandimalla et al., "Mixed Backbone Antisense Oligonucleotides: Design, Biochemical and Biological Properties of Oligonucleotides Containing 2'–5'–ribo– and 3'–5'–Deoxyribonucleotide Segments" *Nucleic Acids Research* 25(2):370–378, 1997.

Lamond and Sproat, "Antisense Oligonucleotides Made of 2'–O–alkylRNA: Their Properties and Applications in RNA Biochemistry" *FEBS* 325(1,2):123–127, Jun. 1993.

Larrouy et al., "RNase H is Responsible for the Non–Specific Inhibition of in vitro Translation by 2'–O–alkyl Chimeric Oligonucleotides: High Affinity or Selectivity, a Diemma to Design Antisense Oligomers" *Nucleic Acids Research* 23(17):3434–3440, 1995.

Lima et al., "The Influence of Antisense Oligonucleotide–Induced RNA Structure on *Escherichia coli* RNase H1 Activity" *J. Biological Chemistry* 272:18191–18199, Jul. 18, 1997.

Lima and Crooke, "Binding Affinity and Specificity of *Escherichia coli* RNase H1: Impact on the Kinetics of Catalysis of Antisense Oligonucleotide–RNA Hybrids" *Biochemistry* 36:390–398, 1997.

Li et al., "Sythesis and Properties of Second–Generation 2–5A–Antisense Chimeras with Enhanced Resistance to Exonucleases" *J. Medicinal Chemistry* 40(18):2959–2966, 1997.

Lonnberg and Vuorio, "Towards Genomic Drug Therapy with Antisense Oligonucleotides" *Ann. Med.* 28:511–522, 1996.

Marcusson et al., "Phosphorothioate Oligodeoxyribonucleotides Dissociate from Cationic Lipids Before Entering the Nucleus" *Nucleic Acids Research* 26(8):2016–2023, 1998.

Marte and Downward, "PKB/Akt: Contecting Phosphoinositide 3–Kinase to Cell Survival and Beyond" *TIBS* 22:355–358, Sep., 1997.

Mitsuhashi, "Strategy for Designing Specific Antisense Oligonuclotide Sequences" *J. Gastroenterol.* 32:282–287, 1997.

Monia et al., "Evaluation of 2'–Modified Oligonucleotides Containing 2'–Deoxy Gaps as Antisense Inhibitors of Gene Expression" *J. Biological Chemistry* 268(19):14514–14522, 1993.

Metelev et al., "Influence of Probe Structure on Unique (regiospecific) Cleavage of RNA by RNase H" *FEBS* 226(2):232–234, Jan., 1988.

Yu et al., "Hybrid Oligonucleotides: Synthesis, Biophysical Properties, Stability Studies, and Biological Activity" *Bioorganic and Medicinal Chemistry* 4(10):1685–1692, 1996.

Shen et al., "Impact of Mixed–Backbone Oligonucleotides on Target Binding Affinity and Target Cleaving Specificity and Selectivity by *Escherichia coli* RNase H" *Bioorganic and Medicinal Chemistry* 6:1695–1705, 1998.

Shibahara et al., "Site–Directed Cleavage of RNA" *Nucleic Acids Research* 15(11):4403–4415, 1987.

Uhlmann and Peyman, "Antisense Oligonucleotides: A New Therapeutic Principle" *Chemical Reviews* 90(4):544–584, Jun., 1990.

Xiao et al., "Nuclease–Resistant Composite 2', 5'–Oligoadenylate–3', 5'–Oligonucleotides for the Targeted Destruction of RNA: 2–5A–Iso–Antisense" *J. Med. Chem.* 41:1531–1539, 1998.

Yamakawa et al., "Properties of Nicked and Circular Dumbbell RNA/DNA Chimeric Oligonucleotides Containing Antisense Phosphodiester Oligodeoxynucleotides" *Bioorganic and Medicinal Chemistry* 6:1025–1032, 1998.

* cited by examiner

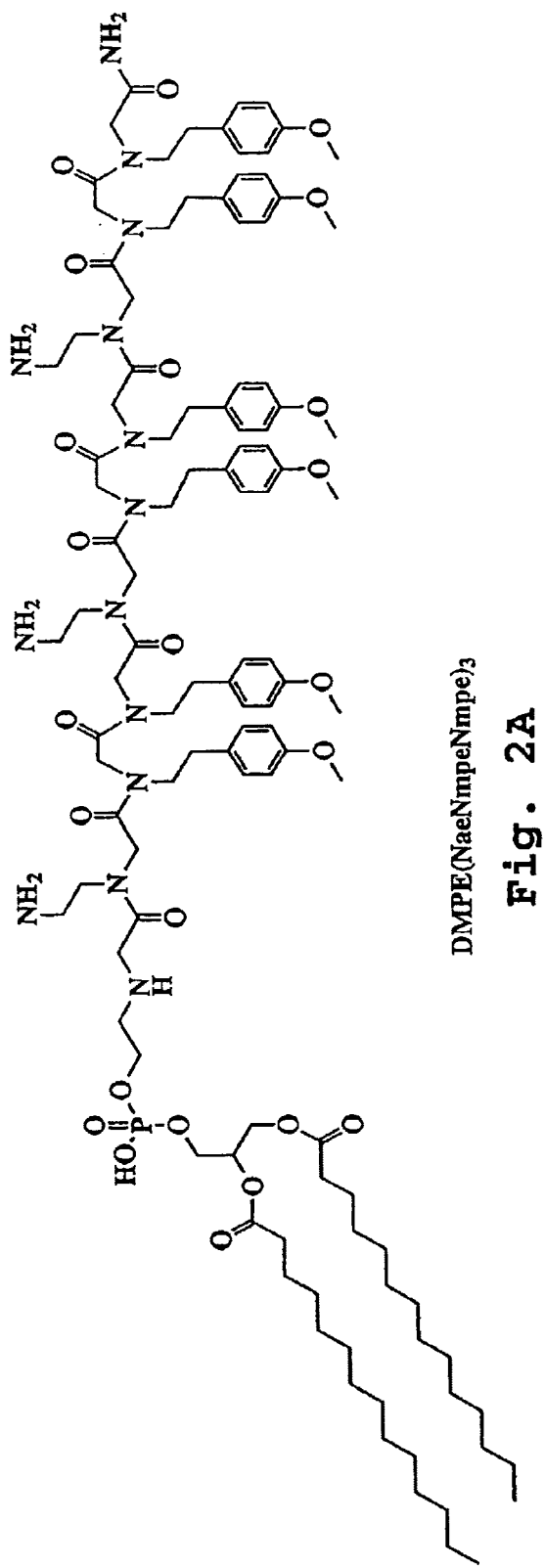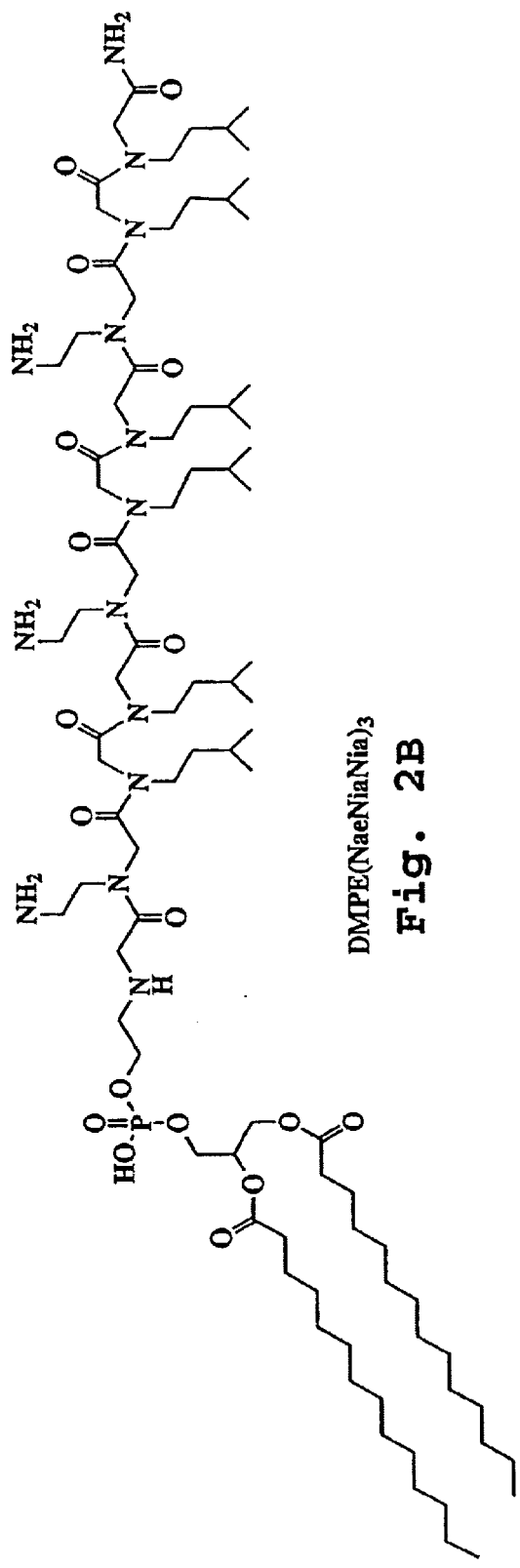
DMPE(NaeNmpeNmpe)₃
Fig. 2A
DMPE(NaeNiaNia)₃
Fig. 2B

Chol-β-ala-(NaeNmpeNmpe)₃

Chol-Ahx-(NaeNmpeNmpe)₃

Chol-β-ala(NaeNiaNia)₃

Chol-Ahx-(NaeNiaNia)₃

CHIMERIC ANTISENSE OLIGONUCLEOTIDES AND CELL TRANSFECTING FORMULATIONS THEREOF

This application claims priority to U.S. provisional application Ser. No. 60/151,246, filed Aug. 27, 1999, which is hereby incorporated by reference in its entirety and for all purposes.

FIELD OF THE INVENTION

The present invention relates to antisense oligonucleotides, and more particularly to chimeric antisense oligonucleotides which exhibit high resistance to endo- and exonucleases, high sequence specificity, and the ability to activate RNAse H, as evidenced by efficient and long-lasting knockout of target mRNA. Also provided are formulations of the oligonucleotides with carrier molecules which provide efficient transfection into cells.

BACKGROUND OF THE INVENTION

The use of antisense oligonucleotides to specifically inhibit the function of targeted genes has been the subject of extensive research, due to its promise in selective antiviral and anticancer therapy. Many studies have been directed to the design of oligonucleotide analogs having an optimal combination of properties, including stability (i.e. resistance to cellular nucleases), cellular uptake, DNA/RNA binding affinity and specificity, and efficiency of inhibition. Because the phosphodiester linkages of native nucleic acids are degraded by endo- and exonucleases, many early studies were directed to designing nuclease-resistant analogs. Phosphorothioates are one such class of compounds, which are relatively stable in vivo and retain the ability to activate RNAse H, the primary mechanism by which antisense oligonucleotides deactivate target RNA. However, the use of phosphorothioates presents several disadvantages, including a high level of non-specific binding to other cellular components, often leading to unwanted side effects, and reduced binding affinity for RNA.

Oligomeric ribonucleotides substituted at the 2'-oxygen show high RNA binding affinities and, in comparison to the unsubstituted ribonucleotides, reduced sensitivity to endogenous nucleases. Although 2'-O-methyl substituted ribonucleotides provide greater binding affinity than those having larger substituents (e.g. ethyl, propyl, pentyl, allyl), the larger substituents are reported to confer greater exonuclease resistance (see, for example, Monia et al., *J. Biol. Chem.* 271(24): 14533, 1996). Arrow et al. (U.S. Patent No. 5,849,902) stated that "2'-O-methyl bases with phosphodiester linkages are degraded by exonucleases and so are not suitable for use in cell or therapeutic applications of antisense." Phosphorothioate and phosphotriester linkages were recommended by the latter group as having greater stability, even though they presented the disadvantages of reduced binding affinity, more difficult synthesis (phosphotriester) and/or greater toxicity (phosphorothioate).

Therefore, there is still a need for antisense oligonucleotide compositions with optimal combinations of antisense activity, target binding affinity, biocompatibility, and stability.

SUMMARY OF THE INVENTION

The present invention includes, in one aspect, a chimeric oligonucleotide having the formula 5'-W-$X^1$-Y-$X^2$-Z-3', where W represents a 5'-O-alkyl nucleotide, such as a 5'-O-alkyl thymidine; each of $X^1$ and $X^2$ represents a block of seven to twelve phosphodiester-linked 2'-O-alkyl ribonucleotides; Y represents a block of five to twelve phosphorothioate-linked deoxyribonucleotides; and Z represents a blocking group effective to block nuclease activity at the 3' end of the oligonucleotide. In one embodiment, Z is a 3-to-3' linked nucleotide. In further embodiments, the alkyl groups of the 5'-O-alkyl nucleotide and/or the 2'-O-alkyl ribonucleotides are methyl groups. In still further embodiments, groups W and/or Z are linked to $X^1$ and $X^2$, respectively, via phosphodiester linkages, phosphotriester, phosphorothioate, or phosphoramidate linkages. Preferably, W is linked via a phosphodiester or phosphorothioate linkage, and Z is linked via a relatively nuclease-resistant linkage; i.e. a phosphotriester, phosphorothioate, or phosphoramidate linkage.

In specific embodiments, the segment $X^1$-Y-$X^2$ of the chimeric oligonucleotide has a sequence represented by any of SEQ ID NOs: 1–24 disclosed herein.

In another aspect, the invention provides a therapeutic composition which comprises an oligonucleotide as described above in a pharmaceutically acceptable vehicle. In preferred embodiments, the vehicle includes a lipid-cationic peptoid conjugate or "lipitoid". One class of lipid-cationic peptoid conjugates includes compounds of the formula:

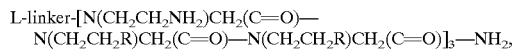

L-linker-[N(CH$_2$CH$_2$NH$_2$)CH$_2$(C=O)—N(CH$_2$CH$_2$R)CH$_2$(C=O)—N(CH$_2$CH$_2$R)CH$_2$(C=O)]$_3$—NH$_2$, where the lipid group L is a fatty acid-derived group, such as a phospholipid group (i.e. ROOCCH$_2$CH(COOR)CH$_2$OP(O)$_2$O—), having fatty alkyl or alkenyl chains between about 8 and 24 carbon atoms in length, or a steroid-derived group, such as a cholesteryl group, and the portion of the molecule to the right of the linker is the peptoid segment. In the peptoid segment, R is selected from alkyl (branched or unbranched), aminoalkyl, and aralkyl. As used herein, "aralkyl" refers to an alkyl, preferably lower alkyl, substituent which is further substituted with an aryl group; one example is a benzyl group. "Aryl" refers to a substituted or unsubstituted monovalent aromatic radical having a single ring (e.g., benzene) or two condensed rings (e.g., naphthyl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a substituent, preferably selected from a halide, a lower alkyl or lower alkoxy group, halomethyl, or haloethyl.

In specific embodiments, R is isopropyl or 4-methoxyphenyl. A single lipitoid may include different groups R, or they may be the same within the molecule.

The linker may be a direct bond, or it may be a substantially linear linking group, such as an oligopeptide or an alkyl chain, of any effective length. The linker may also be an alkyl chain having one or more heteroatom-containing linkages, selected from the group consisting of ester, amide, carbonate, carbamate, disulfide, peptide, and ether, at either terminus of the chain or intervening between alkyl bonds. In selected embodiments, the linker is from 2 to about 30 atoms, or from 3 to about 15 atoms, in length.

In another aspect, the invention provides a method of inhibiting expression of a target gene in a subject, which comprises administering to the subject, in a pharmaceutically acceptable vehicle, an amount of a chimeric oligonucleotide effective to specifically hybridize to all or part of a selected target nucleic acid sequence derived from the gene, where the chimeric oligonucleotide has a structure as described above. In one embodiment, the target nucleic acid sequence is a mRNA derived from the target gene. In specific embodiments, the segment $X^1$-Y-$X^2$ of the chimeric oligonucleotide has a sequence represented by any of SEQ ID NOs: 1–24 disclosed herein. In further embodiments, the vehicle includes a lipid-cationic peptoid conjugate such as described above.

As shown herein, the chimeric oligonucleotides of the invention provided surprisingly high stability and efficient and long-lasting knockout of target mRNA. These and other objects and features of the invention will become more fully apparent when the following detailed description of the invention is read in conjunction with the accompanying drawings.

DETAILED DESCRIPTION OF THE INVENTION

I. Chimeric Antisense Oligonucleotides
A. Structure
The chimeric oligonucleotides of the invention have the general structure shown below:

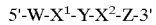

In this structure, the central portion of the molecule, represented by Y, is a block of between five and twelve phosphorothioate-linked deoxyribonucleotides (phosphorothioate DNA, or PS DNA). In one embodiment, the block Y is effective to activate RNAse H when hybridized to a sufficiently complementary strand of RNA, thus promoting cleavage of the RNA. Block Y is flanked by two binding blocks, represented by $X^1$ and $X^2$, each having between seven and twelve phosphodiester-linked 2'-O-alkyl ribonucleotide subunits (phosphodiester 2'-O alkyl RNA, or PO 2'-O-alkyl RNA). As used herein, "alkyl" refers to a fully saturated acyclic monovalent radical containing carbon and hydrogen, which may be branched or a straight chain; examples of alkyl groups are methyl, ethyl, n-butyl, t-butyl, n-heptyl, and isopropyl. "Lower alkyl" refers to an alkyl radical of one to six carbon atoms, and preferably one to four carbon atoms.

The alkyl groups of the 2'-O-alkyl ribonucleotide subunits are preferably lower alkyl groups. In one embodiment, the alkyl groups are methyl groups, which provide generally superior binding and cellular uptake in comparison to longer alkyl groups. The binding blocks, while not necessarily effective to participate in activation of RNAse H, provide binding affinity to sufficiently complementary RNA strands and may also provide reduced cellular toxicity compared to phosphorothioate-linked subunits.

Blocking groups Z and W are provided at the 3' and 5' termini, respectively. In one embodiment, the groups W and Z are linked to the respective X blocks by phosphodiester linkages; in another embodiment, they are attached via phosphorothioate linkages. The 3'-blocking group Z is preferably a 3'-to-3' linked nucleotide, although this terminus may also be blocked by other methods, e.g. by attachment of the terminal nucleotide via a relatively nuclease-stable linkage (e.g. phosphorothioate, phosphoramidate, phosphotriester) or appendage of a non-nucleotide moiety.

The 5'-terminus is blocked with a 5'-O-alkyl nucleotide subunit (W), where alkyl is preferably lower alkyl. In one embodiment, W is a 5'-O-methyl thymidine. This blocking group is found to confer stability to the chimeric oligonucleotides in cell culture and in serum. For example, the duration of MRNA knockout in cell cultures (discussed further below) typically ranged from 3–5 days post transfection. In addition to providing stability, this blocking group, and the 3'-to-3' nucleotide blocking group, were found not to interfere with uptake or distribution of the oligonucleotides.

Figure 1:
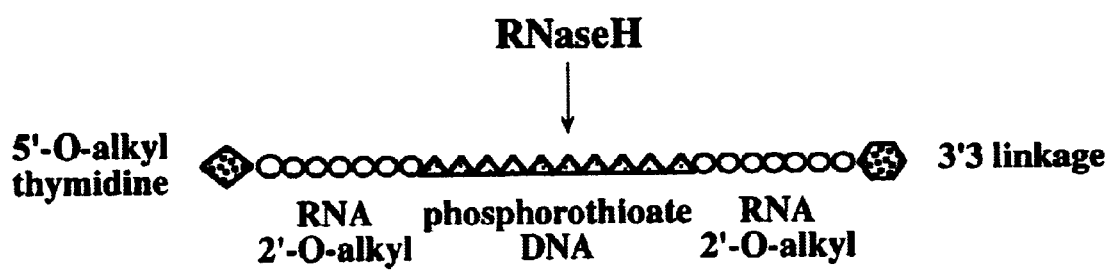
FIG. 1 shows a schematic representation of a chimeric oligonucleotide, in accordance with one embodiment of the invention.
Figure 2C:
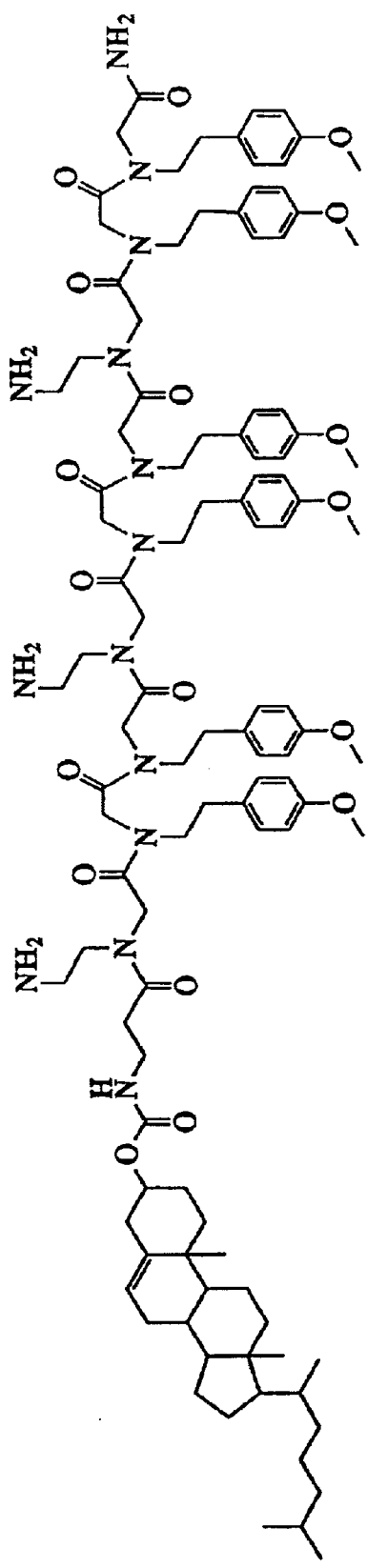
FIG. 2 shows a selection of phospholipid-peptoid conjugates ("lipitoids") and cholesterol-peptoid conjugates ("cholesteroids") useful as oligonucleotide carriers in compositions and methods of the invention.
Figure 2D:
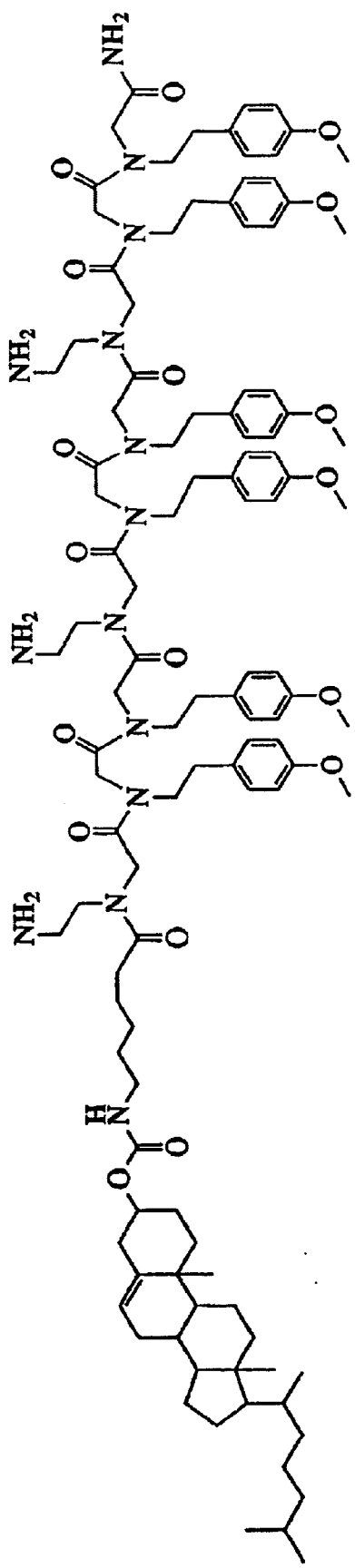
Figure 2E:
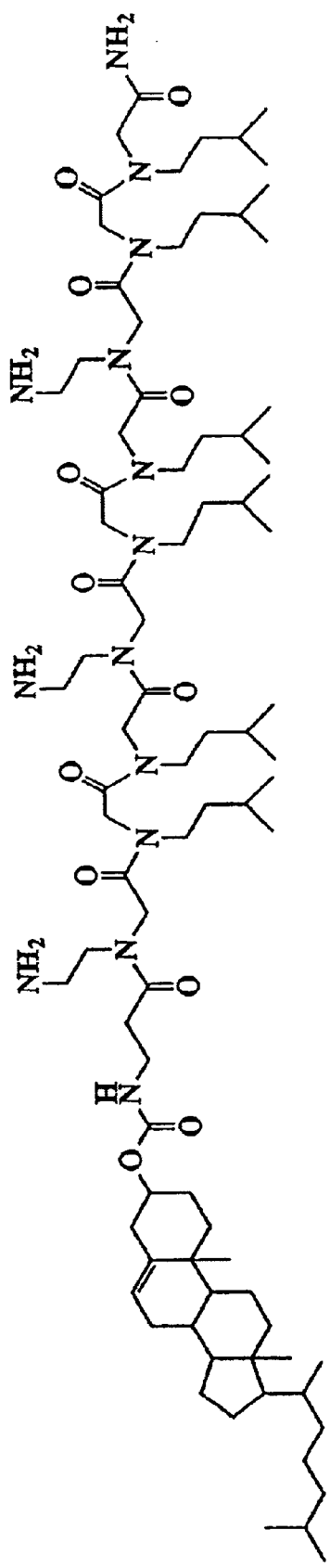
Figure 2F:
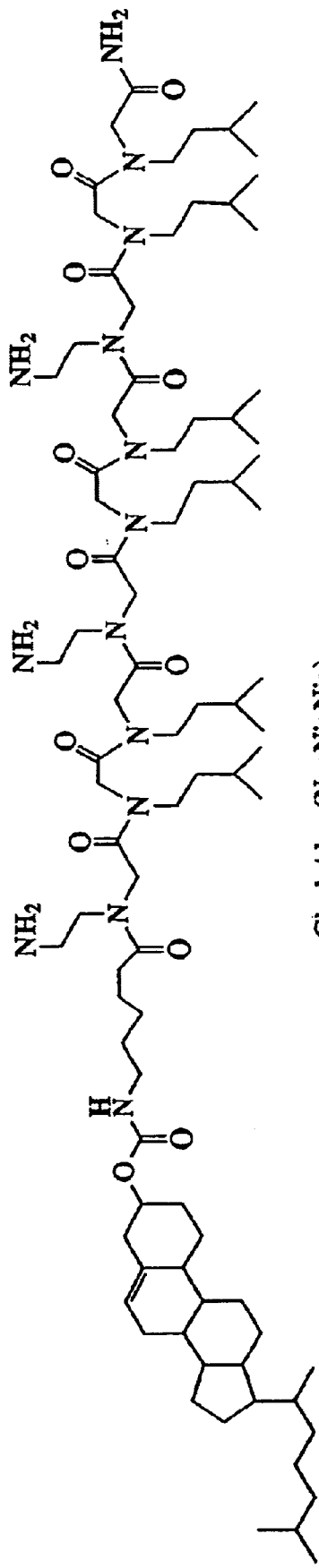

The chimeric oligonucleotides of the invention can be prepared using solution phase or, preferably, solid phase synthesis, according to established procedures. Synthesis of an exemplary chimeric oligonucleotide, such as shown in FIG. 1, is described in Example 1.
B. Antisense Activity
Antisense chimeric oligonucleotides based on the formula above, having sequences directed against AKT1 (SEQ ID NO: 1) or AKT2 (SEQ ID NO: 2), were prepared as described in Example 1. The oligonucleotides also included a 5'-terminal 5'-O-methyl thymidine, as indicated by the formula above. In these oligonucleotides, $X^1$ and $X^2$ were seven-base blocks of 2'-O-methyl PO RNA, Y is PS DNA, Z was a 3'-to-3' linked nucleotide, and W was a 5'-O-methyl thymidine. Both Z and W were linked to the respective X blocks via phosphodiester linkages. When transfected into cells as described in Example 2, chimeric antisense oligonucleotides of the invention having various sequences (see Table 1) showed surprisingly effective degradation of endogenous mRNA, resulting in a loss of activity of the respective genes. FIGS. 5 and 6 show levels of endogenous AKT1 MRNA in colon cancer cells and HT1080 cells, respectively, transfected with anti-AKT1 chimeric oligonucleotides (SEQ ID NO: 1). Similarly, a chimeric antisense oligonucleotide directed against hCHK1 (SEQ ID NO: 3) showed degradation of endogenous mRNA, loss of chk1 kinase activity, and loss of chk1 function (i.e. G2 cell cycle checkpoint control).

Additional chimeric oligonucleotides having the sequences shown in Table 1 were prepared and administered to cells as described in Example 2. (Each oligonucleotide included a 5'-O-methyl thymidine, as described above, which is not shown in the listed sequences.) In these oligonucleotides, with reference to the formula above, $X^1$ and $X^2$ are seven-base blocks of 2'-O-methyl PO RNA, Y is a nine- to eleven-base block of PS DNA, Z is a 3'-to-3' linked nucleotide, and W is a 5'-O-methyl thymidine. Both Z and W are linked via phosphodiester linkages.

With the exception of the mTyr oligo (SEQ ID NO: 17–18), which was transfected into B16 melanoma cells, all oligos shown in Table 1 were transfected into T1080 cells, using "Lipitoid 1" (see below) for transfection, and incubated for 24 hours. The table gives the approximate level of mRNA knockout observed in each case. Reduction in mRNA levels of 90% or more were frequently observed, as shown in the Table.

for example, in co-owned PCT publications WO 98/06437 and WO 99/08711 (Zuckermann et al.), based on U.S. Ser. Nos. 60/023,867, 60/054,743, and 09/132,808, which are hereby incorporated by reference. These lipid-cationic peptoid conjugates are shown in these references to be effective reagents for the delivery of plasmid DNA to cells in vitro. It is shown herein that such compounds efficiently deliver oligonucleotides into a variety of primary and tumor cell lines. The efficiency of delivery was assessed by fluorescence analysis of FITC-labeled oligonucleotides, or by monitoring mRNA levels after transfection of chimeric antisense oligonucleotides, as described further below.

Any of the carriers described in the above-referenced applications are suitable for use in transfection of the oligonucleotides described herein. Further disclosure of

TABLE 1

| SEQ ID NO: | Antisense Oligonucleotide Sequence ($X^1$-Y-$X^2$ Segment) | Gene | Nucleotide Position in Gene | Locus/Acc for Genbank | mRNA knockout |
|---|---|---|---|---|---|
| 1 | CCATAGTGAGGTTGCATCTGGTGCC | AKT1 | AKT1-2074 | NM005163 | >90% |
| 2 | GTTCCCTTGCCAAGGAGTTTGAGAT | AKT2 | AKT2-548 | NM001626 | >85% |
| 3 | CCCAGAGCCGATGGTCCGATCATGT | CHK1 | CHK1-1460 | CHEK1 | >90% |
| 4 | GACCCACTTCCCTGAAAATCCGAAA | CHK2 | CHK2-430 | AF086904 | >90% |
| 5 | CGGCGTTTTCCTTTCCCTACAAGC | | CMK2-518 | AF086904 | |
| 6 | AGCGGCAGAAGTTGAGGTATGTTGA | CK1E | CK1E-766 | HUMCSNK1E | >80% |
| 7 | CCTGCCAGTATGAAGTTGGGAAGCG | E1AF | E1AF-1729 | HUME1AF | >90% |
| 8 | GCGAAGTCCGTCTGTTCCTGTTTGA | | E1AF-710 | HUME1AF | |
| 9 | TCTTCCTCACAGACCTTCGGGCAAG | IGFR1 | IGF1R-1025 | HSIGFIRR | >80% |
| 10 | TGCTGATAGTCGTTGCGGATGTCG | | IGF1R-156 | HSIGFIRR | |
| 11 | GTGTTTGTTCAGGGTTCCATTTCGG | ILK | ILK-687 | HSU40282 | >90% |
| 12 | GCATGTGGAAGGTAGGGAGGCAAGA | KRAS | KRAS-2576 | HUMKRASM | >85% |
| 13 | ACCATATACCCAGTGCCTTGTGCGG | | KRAS-3352 | HUMKRASM | |
| 14 | GAAGCCCCACTTGCGGTCGTCAT | MMP2 | MMP2-1098 | HUMCN4GEL | >80% |
| 15 | ACGAGCAAAGGCATCATCCACTGTC | | MMP2-367 | HUMCN4GEL | |
| 16 | GCTTTCTCTCGGTACTGGAAGACGT | MMP9 | MMP9-2007 | HUM4COLA | >80% |
| 17 | AACCCATGAAGTTGCCTGAGCACTG | mTyr | MTYR-332 | MUSTYR | >90% |
| 18 | TTTCAGGGTGACGACCTCCCAAGTA | | MTYR-814 | MUSTYR | |
| 19 | ATCTGGTCGCCTCATTTGCTCAACT | p110α | P110A-2205 | HSU79143 | >95% |
| 20 | TTTCTTCACGGTTGCCTACTGGTTC | | P110A-307 | HSU79143 | |
| 21 | TGATGAAGAGATTCCCATGCCGTCG | p110β | P110B-2980 | S67334 | >90% |
| 22 | TGTAGTCTTTCCGAACTGTGTGGGC | | P110B-3181 | S67334 | |
| 23 | CTGTGAGCAACAGCTGTCGTCGTCT | PDK1 | PDK1-1494 | NM002613 | >90% |
| 24 | GGCAGTCATTAGCAGGGTGATGGTG | UPAR | UPAR-1242 | HSU08839 | >80% |

II. Transfection Agents

A variety of strategies exist for delivery of nucleic acid compositions to cells. Viral vectors provide relatively efficient delivery, but in some cases present safety problems due to the risk of immunological complications or unwanted propagation in the subject. Adenoviral vectors have shown certain advantages in that they do not integrate into the genome of the cell and can be transduced into resting cells. However, all of these vectors must be prepared by time consuming recombinant DNA techniques. Oligonucleotides may also be delivered to cells via chemical transfection agents, which have been the subject of much recent work. These agents include polycationic molecules, such as polylysine, and cationic lipids. The liposomal composition Lipofectin® (Felgner et al., PNAS 84:7413, 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. Any of these methods, as well as other methods such as calcium phosphate mediated transfection, can be used to deliver the oligonucleotides of the invention, according to reported procedures.

One method of delivery involves the use of transfection agents known as "lipitoids" and "cholesteroids", described, steroids useful for incorporating into steroid-cationic peptoid conjugates is found in PCT publication WO 97/46223 (Fasbender et al.) and corresponding U.S. Pat. No. 5,935,936, which are hereby incorporated by reference.

These compounds may be prepared by conventional solution or solid-phase synthesis. In one such procedure, as described in Zuckermann et al., cited above, the N-terminus of a resin-bound peptoid is acylated with a spacer such as Fmoc-aminohexanoic acid or Fmoc-β-alanine. After removal of the Fmoc group, the primary amino group is reacted with cholesterol chloroformate to form a carbamate linkage, e.g. as shown in Cholesteroids 2, 3, and 4 of FIG. 2. The product is then cleaved from the resin with trifluoroacetic acid and purified by reverse-phase HPLC. A fatty acid-derived lipid moiety, such as a phospholipid, may be used in place of the steroid moiety, as also shown in FIG. 2.

The steroid or other lipid moiety may also be linked to the peptoid moiety by other linkages, of any effective length, readily available to the skilled practitioner. The linker is a chain up to about 30 bonds in length, and more preferably up to about 15 bonds in length, though any effective length may be used. The chain is typically linear or substantially linear, although branched chains (including oligopeptides) and linkers containing intervening cyclic groups can also be used. The linker generally comprises alkyl (C—C) bonds and one or more functional groups such as ester, amide, carbonate, carbamate, disulfide, peptide or ether bonds. The linker may comprise multiple functional groups, as in a succinate ester or polyether, or it may be an oligopeptide, preferably a 2- to 10-mer, and more preferably a 2- to 5-mer. The steroid or lipid moiety and peptoid segment can also be joined by a direct bond.

In certain embodiments, the linker incorporates one or more bonds which are susceptible to cleavage under appropriate conditions in vivo; for example, hydrolyzable ester, carbonate, carbamate, or peptide bonds; disulfide bonds, which are cleavable in cellular compartments having a sufficiently reducing environment; and peptide bonds, cleavable by endogenous peptidases. With respect to the latter, polypeptide linkers having ten or fewer, or, in further embodiments, five or fewer peptide linkages are contemplated, though longer linkers may also be used.

In particular embodiments, the lipid-cationic peptoid conjugate belongs to a class of compounds having the formula:

L—CH$^2$)$_n$—(C=O)—[N(CH$_2$CH$_2$NH$_2$)CH$_2$(C=O)—
N(CH$_2$CH$_2$R)CH$_2$(C=O)—N(CH$_2$CH$_2$R)CH$_2$(C=O)]$_3$—NH$_2$, where L is selected from (i) a phosphatidylethanolamino group (i.e. ROOCCH$_2$CH(COOR)CH$_2$OP(O)$_2$O—CH$_2$CH$_2$NH$_2$—), having fatty alkyl or alkenyl chains between about 8 and 24 carbon atoms in length, and (ii) a cholesteryl group linked to the adjacent —(CH$_2$)$_n$— segment by an ester, amide or carbamate linkage; n is 1–5; and R is selected from isopropyl and 4-methoxyphenyl. Representative structures of this class, shown in FIG. 2, are given the following designations herein:

| | |
|---|---|
| Lipitoid 1, or L1 | DMPE(NaeNmpeNmpe)$_3$ |
| Lipitoid 2, or L2 | DMPE(NaeNiaNia)$_3$ |
| Cholesteroid 1, or Chol 1 | Chol-β-ala-(NaeNmpeNmpe)$_3$ |
| Cholesteroid 2, or Chol 2 | Chol-Ahx-(NaeNmpeNmpe)$_3$ |
| Cholesteroid 3, or Chol 3 | Chol-β-ala-(NaeNiaNia)$_3$ |
| Cholesteroid 4, or Chol 4 | Chol-Ahx-(NaeNiaNia)$_3$ |

As used herein, the term "lipitoid" may be used generically to include both lipitoids and cholesteroids, unless referring to a particular Lipitoid, such as L1 or L2, above.

To prepare transfecting compositions, an aqueous solution of a peptoid, lipitoid or cholesteroid is formulated with the oligonucleotide, as described in Example 2A. The components are preferably used in relative amounts such that there are at least two, and preferably two to four, positive lipitoid charges for every DNA negative charge. The exact ratio of antisense oligonucleotide to lipitoid is preferably determined empirically for each cell type, but is generally in the range of 1.5–2 nmol lipitoid/μg antisense oligonucleotide. Cells may be transfected as described above and in Example 2B.

The extent of delivery of FITC-labeled chimeric oligonucleotides into human fibrosarcoma (HT1080) cells was assessed via fluorescence analysis. (All oligonucleotides used in the subsequent studies were chimeric oligonucleotides as described for the studies represented in Table 1.) The sequence of the oligonucleotides was the reverse control of PDK1 (SEQ ID NO: 25, the reverse of SEQ ID NO: 23) so that the effect of the oligonucleotides on the cells would be minimal. The oligonucleotides were transfected via complexation with (a) a commercially available transfection agent, Effectene™, (b) the peptoid (NaeNmpeNmpe)$_3$ (peptoid 1), (c) Lipitoid 1, in a 1:4 charge ratio of oligo to lipitoid, and (d) Lipitoid 1, in a 1:3 charge ratio. In comparison to Effectene™, Lipitoid 1 gave a significantly higher transfection efficiency and higher degree of nuclear delivery of the oligonucleotide, as evidenced by fluorescence analysis of the transfected cells. The higher lipitoid/oligo charge ratio (1:4; c) also appeared to be more effective than the 1:3 ratio.

Figure 3:
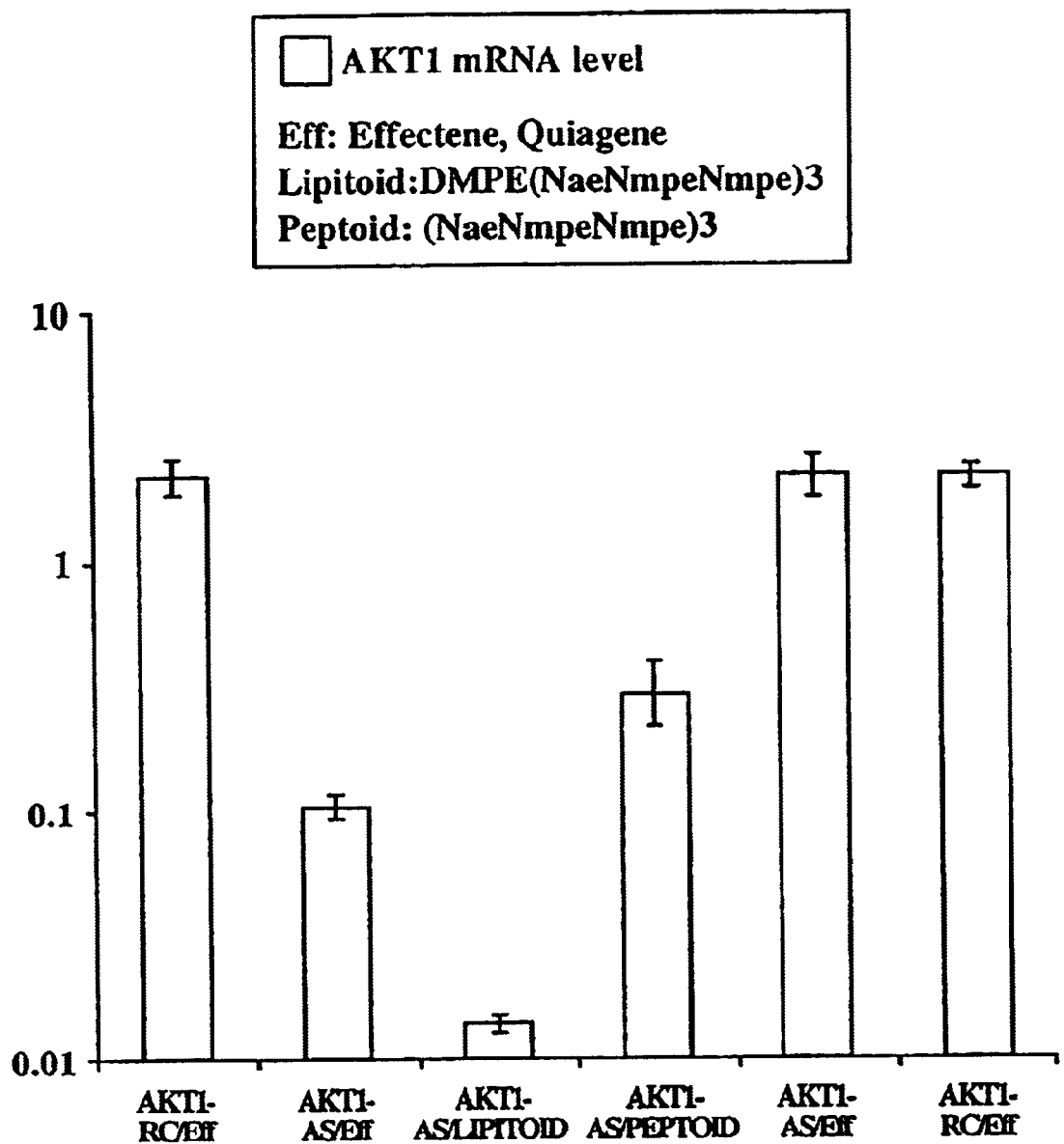
FIG. 3 shows the effect on AKT1 mRNA level of anti-sense oligos to AKT1 delivered to HT1080 cells via Effectene™, Lipitoid 1, and peptoid 1, and control oligos (AKT2-AS, AKT2-RC, and AKT1-RC) delivered via Effectene™.

FIG. 3 shows the reduction in endogenous AKT1 MRNA in HT1080 cells resulting from transfection of a chimeric antisense oligonucleotide to AKT1, as described above (AKT1-AS), in comparison to control oligonucleotides AKT1-RC (RC=reverse control; SEQ ID NO: 26; reverse of SEQ ID NO: 1), AKT2-AS, and AKT2-RC (SEQ ID NO: 27; reverse of SEQ ID NO: 2). The same oligos were also delivered by commercial lipids (Effectene™) and peptoids ((NaeNmpeNmpe)$_3$). The results, depicted in FIG. 3, show that L1-transfected AKT1 chimeric antisense oligonucleotides gave the most pronounced reduction in the target mRNA level.

Figure 4:
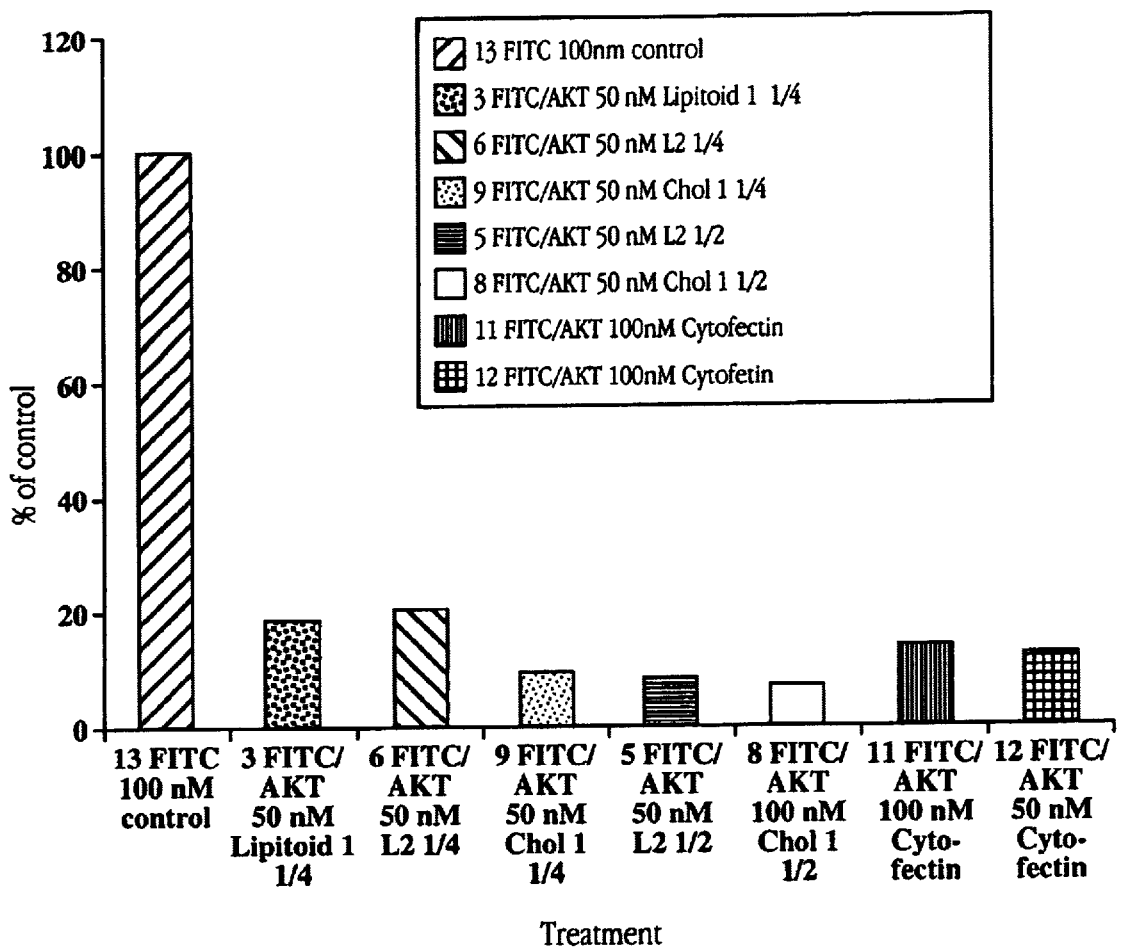
FIG. 4 shows the effect on AKT1 mRNA level of anti-sense oligos to AKT1 delivered to colon cancer cells (Lovo) in conjunction with: Lipitoid 1, two different charge ratios of Lipitoid 2 (DMPE(NaeNiaNia)$_3$), two different charge ratios of Cholesteroid 1 (Chol-β-ala-(NaeNmpeNmpe)$_3$), and the commercially available transfection agent Cytofectin™.

Efficiency of oligonucleotide delivery by cholesteroids has been found to be similar or superior to that of (non-steroid) lipitoids. For example, as shown in FIG. 4, delivery of the chimeric anti-AKT1 oligo described above by Cholesteroid 1 achieved a better AKT1 mRNA knockout than delivery by Lipitoid 1 or Lipitoid 2 in a colon cancer cell line (Lovo).

Figure 5A:
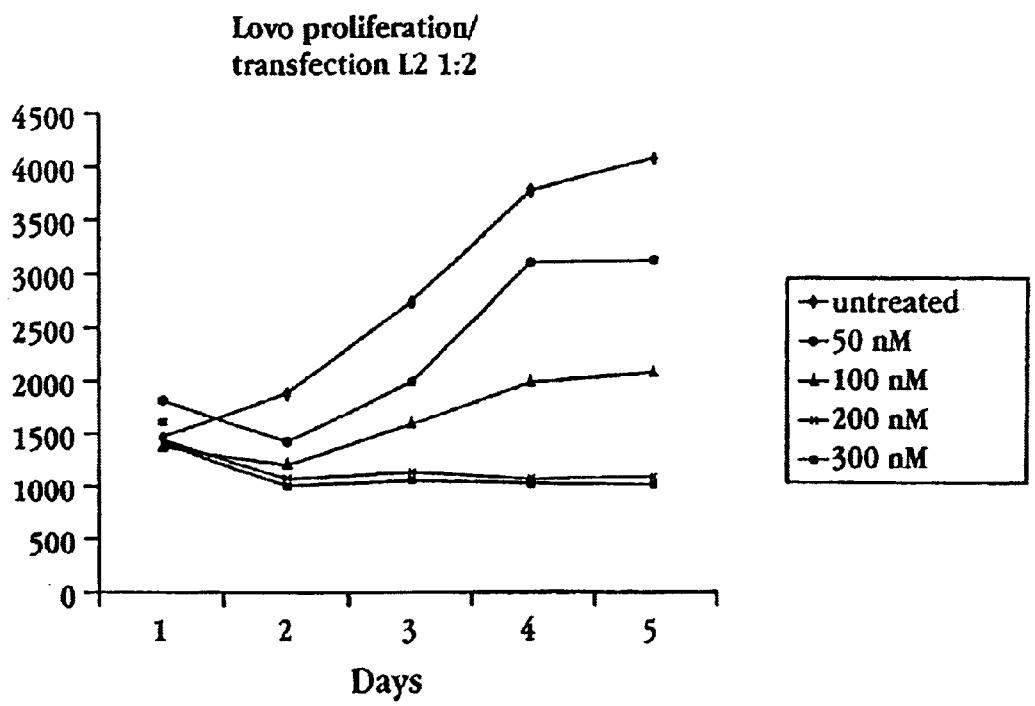
FIGS. 5–7 show the effects on cell proliferation of transfection of Lovo, Km12L4, and Colo320DM colon cancer cells, respectively, with chimeric oligonucleotides of the invention, in conjunction with different lipitoid and cholesteroid carriers.
Figure 5B:
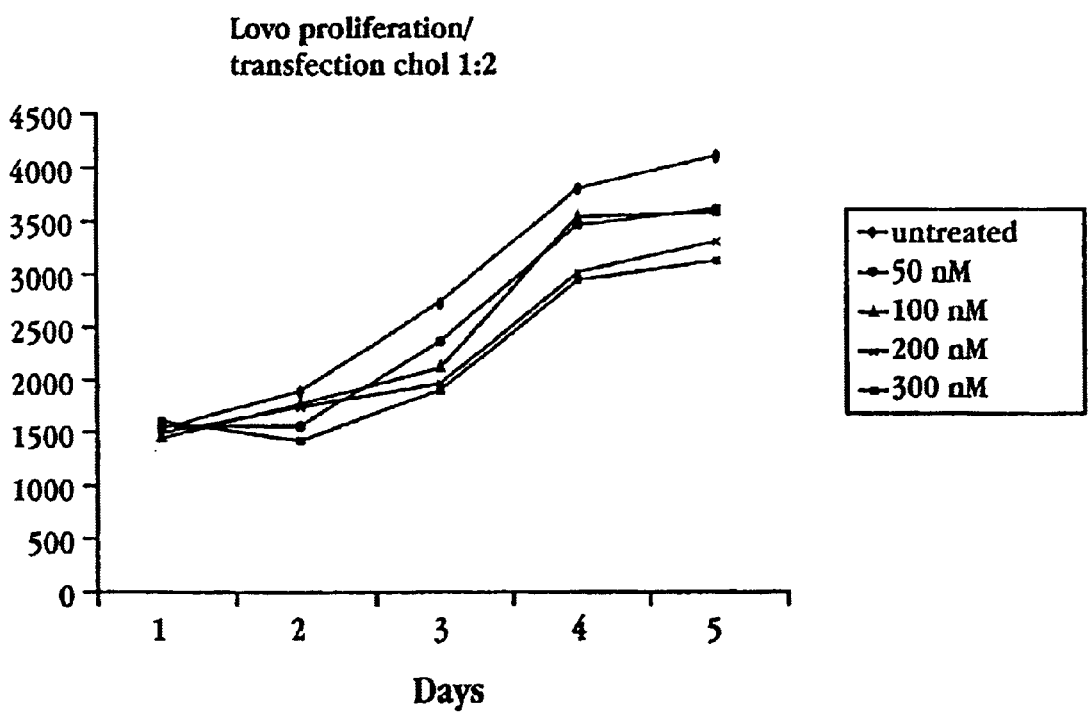
Figure 6A:
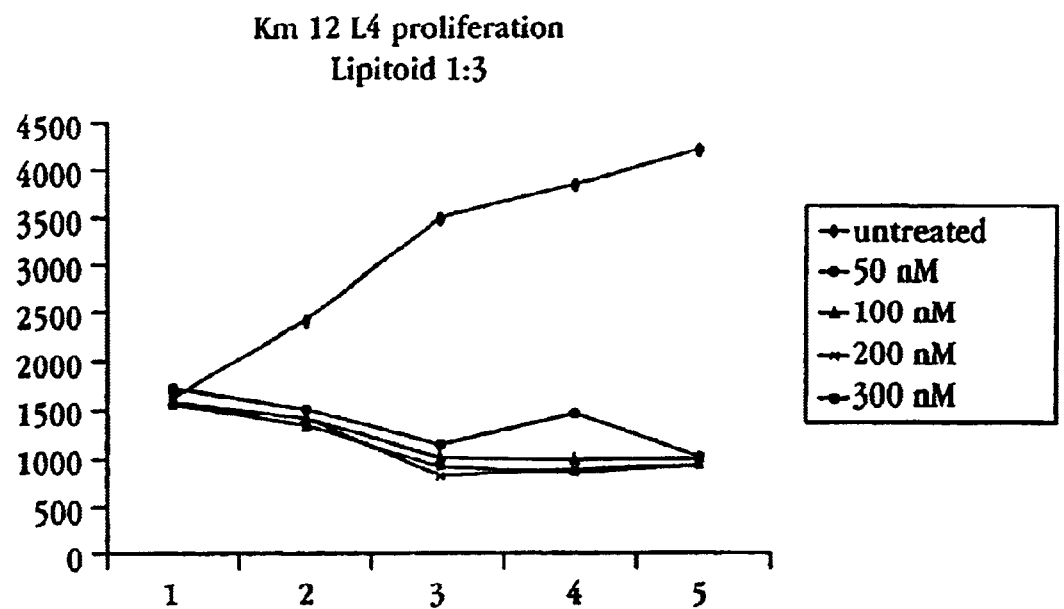
Figure 6B:
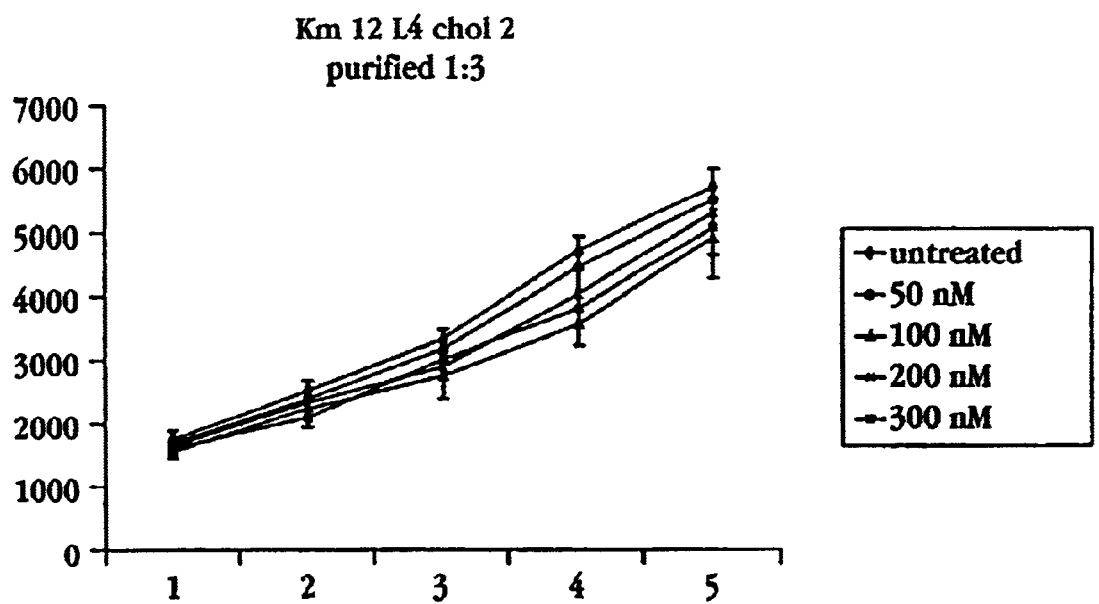
Figure 6C:
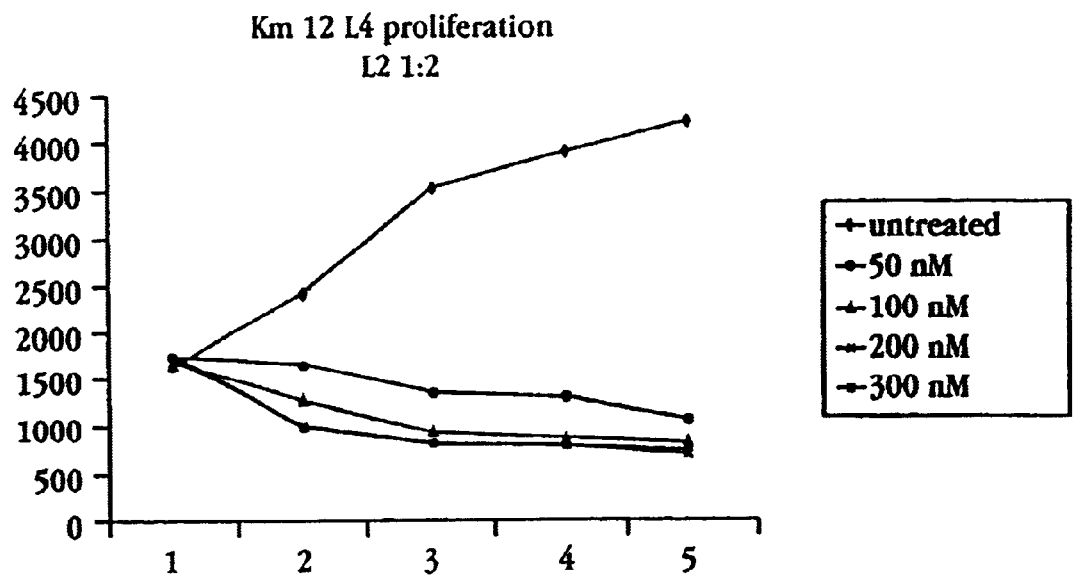
Figure 6D:
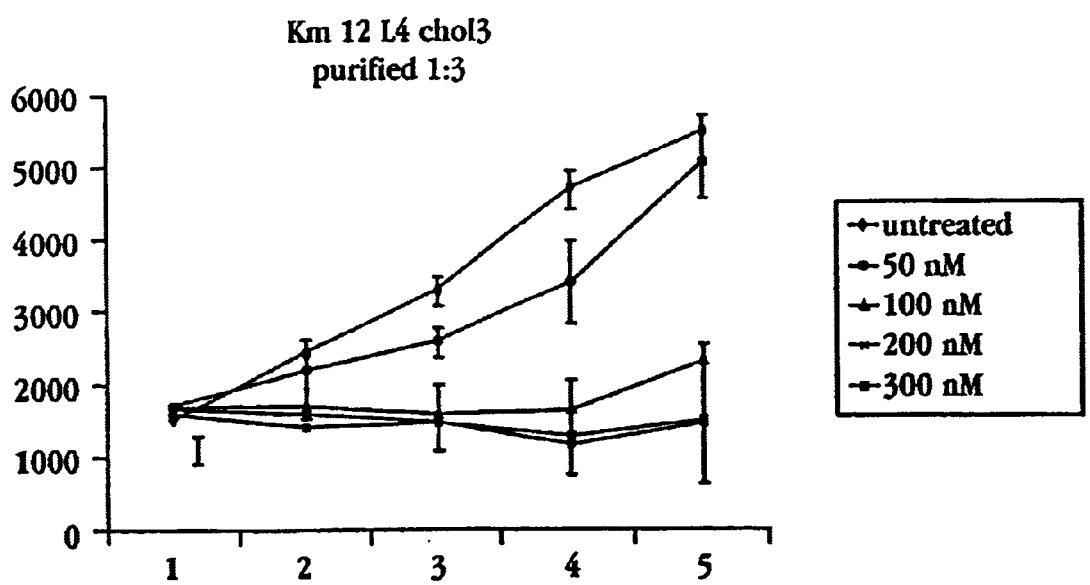
Figure 7A:
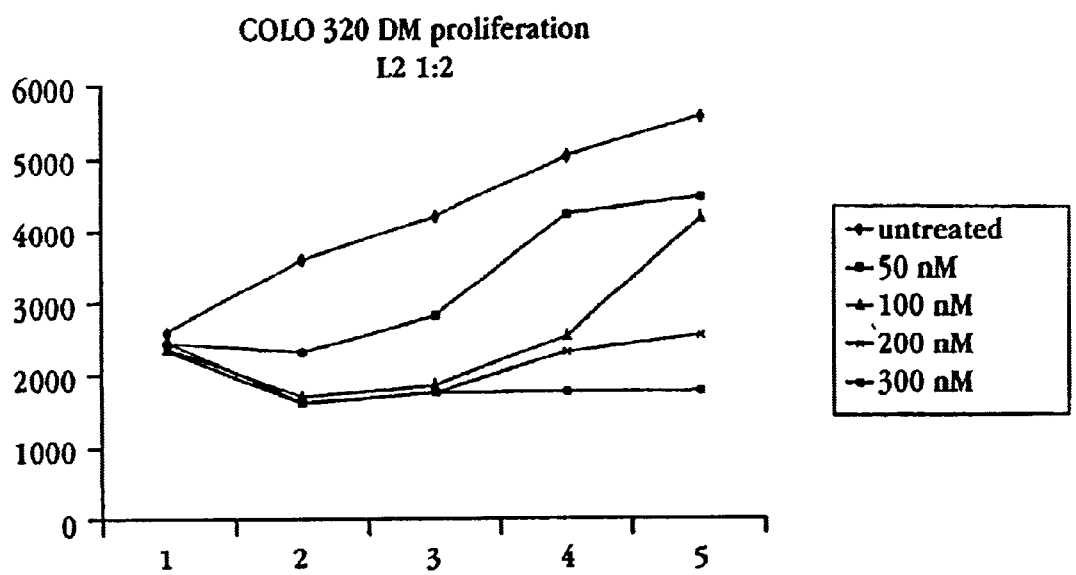
Figure 7B:
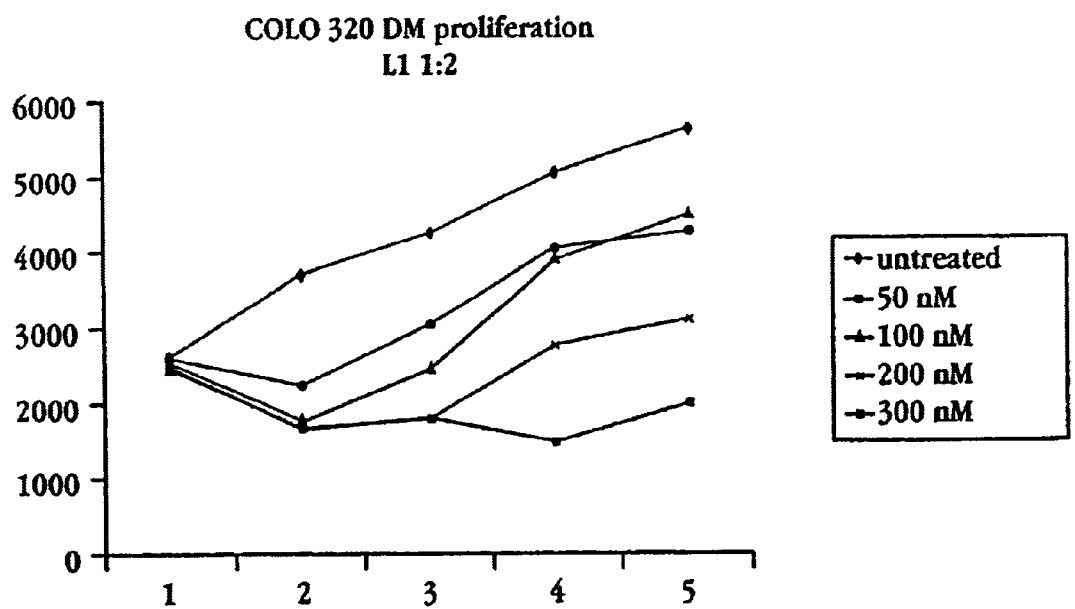
Figure 7C:
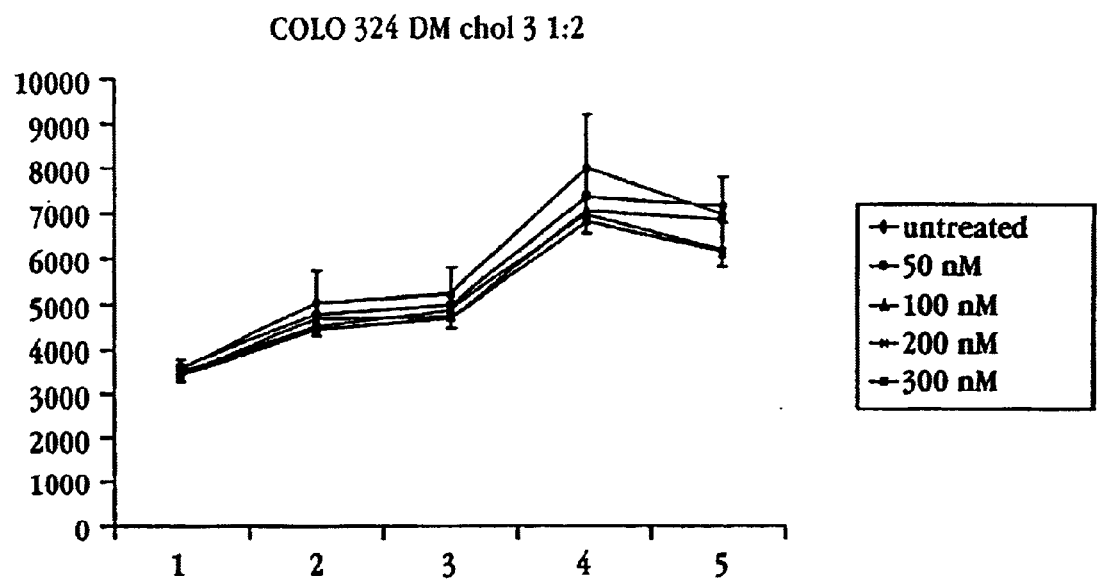
Figure 7D:
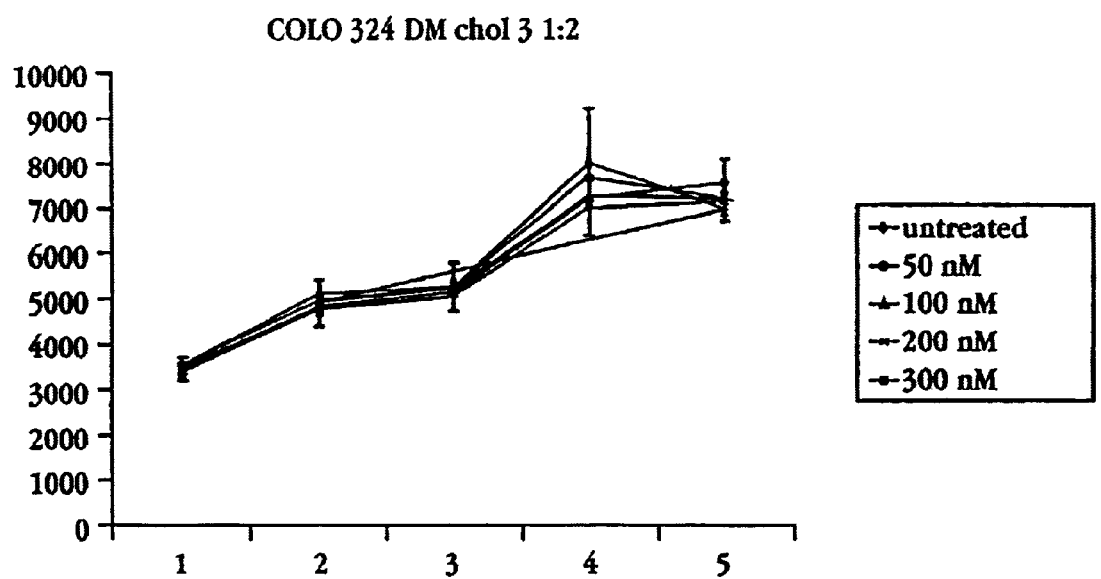

The cholesteroids provide the additional benefit of substantially reduced toxicity to cells in vitro. FIG. 5 shows a 4 day proliferation assay, conducted as described in Example 3, of Lovo colon cancer cells following transfection of 50–300 nM of oligonucleotides. (Again, reverse control PDK1 chimeric oligonucleotides, expected to be non-active, were used.). These charts demonstrate the significant increase in proliferation and viability of the Lovo cells following an oligonucleotide transfection with Cholesteroids 2 and 3 (FIGS. 5B,D) as compared with transfection with Lipitoids 1 and 2 (FIGS. 5A,C). This effect is not limited to this cell type, and was also observed in proliferation assays of Km12L4 colon cancer cells (FIG. 6) and Colo320DM colon cancer cells (FIG. 7).

Figure 8A:
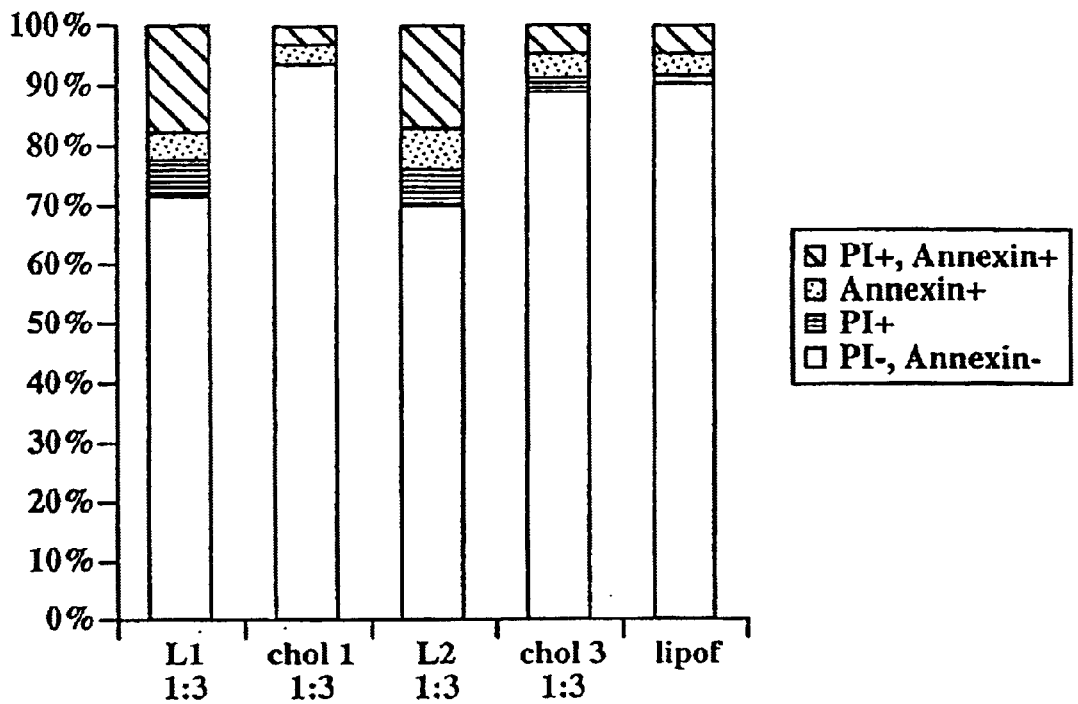
FIG. 8 shows the results of several cell viability assays on Km12L4 and HCT-166 cells transfected with oligonucleotides in conjugation with lipitoids 1 and 2, cholesteroids 1 and 3, and the commercially available transfection agents Lipofectin® and Cytofectin™, where the white regions indicate levels of healthy cells.
Figure 8B:
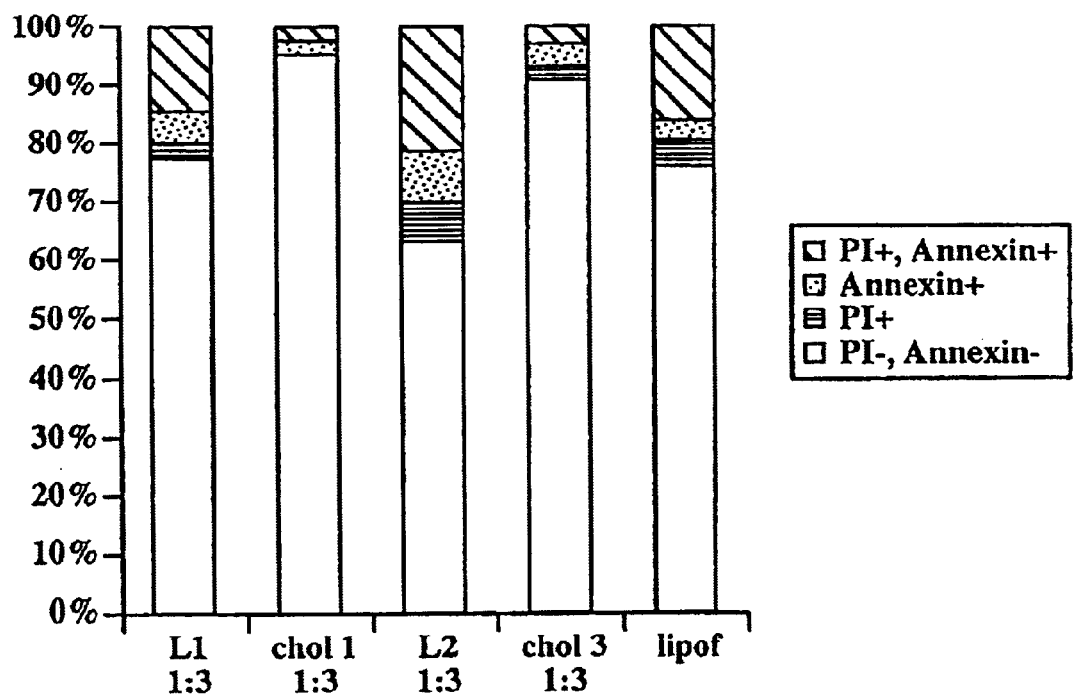
Figure 8C:
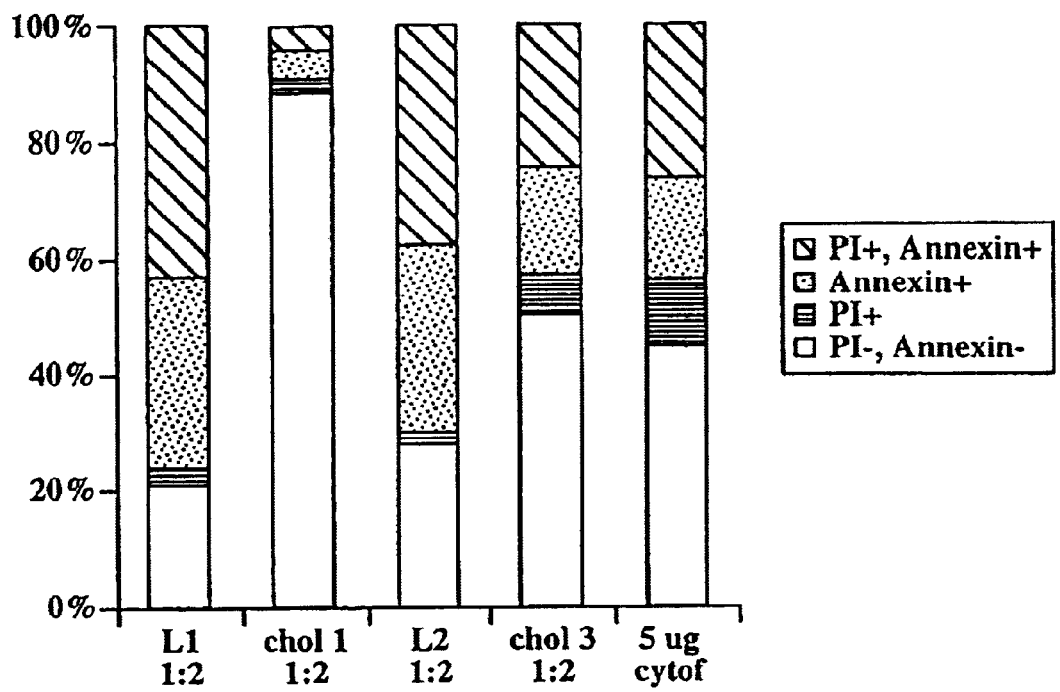
Figure 8D:
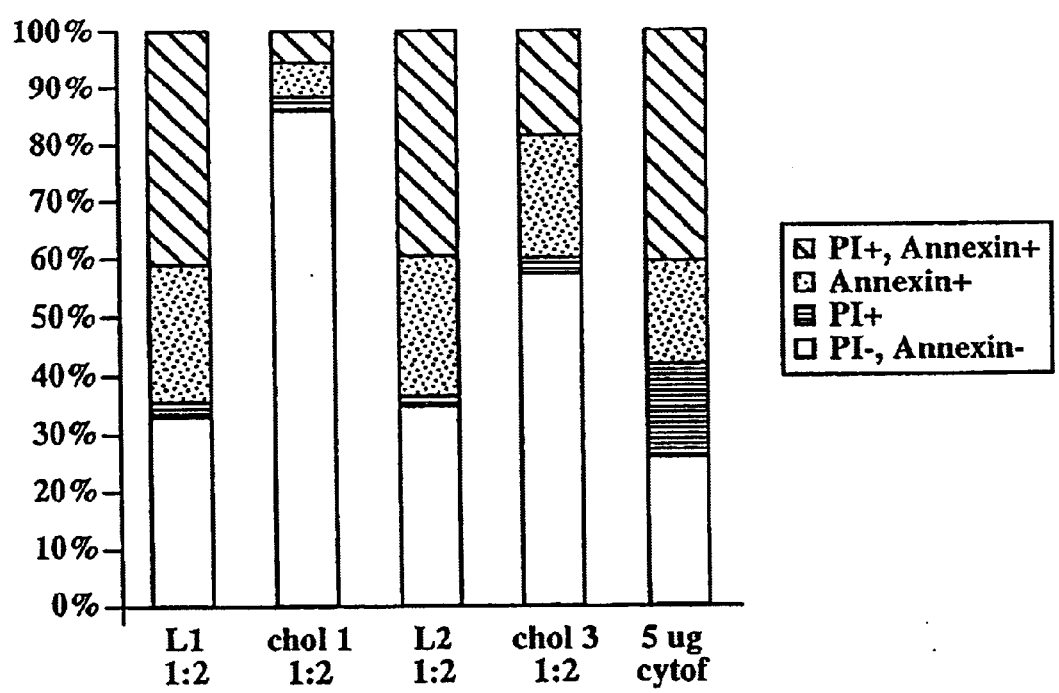

To further investigate the reduced toxicity of the cholesteroids, a FACS analysis of cells was carried out, following transfection (see Example 4), to determine the number of necrotic (PI+), early apoptotic (annexin+), late apoptotic (annexin+/PI+) and healthy cells (annexin−/PI−). The white columns in FIG. 8 reflect the number of healthy cells, while colored portions of the bars (demarcated by short line segments for clarity) represent dead or dying cells. The analysis was performed on Km12L4 (FIGS. 8A–B) and HCT116 cells (FIGS. 8C–D). The percentage of dying cells was determined 4 hours (FIGS. 8A,C) or 24 hours (FIGS. 8B,D) post-transfection. While different cell types show different sensitivity to the transfection, cells transfected with cholesteroids consistently contained the most healthy cells and showed the lowest degree of cell death. This lower toxicity was also seen in comparison of cholesteroids with the commercially available lipids Lipofectamine® and Cytofectin™.

EXAMPLES

The following examples illustrate but are not intended in any way to limit the invention.

Example 1

Synthesis of Chimeric poRNA-psDNA-poRNA Oligonucleotides

The chimeric oligonucleotides were prepared using solid phase synthesis, according to established procedures. A PerSpective Biosystems (Framingham, Mass.) 8909 Synthesizer and an ABI 394 Synthesizer (ABI/Perkin-Elmer, Foster City, Calif.) were used for the RNA additions and the phosphorothioate linked DNA additions, respectively. It is also possible to perform the synthesis using only one instrument with eight amidite reagent bottles. Unless otherwise noted, all reagent preparation and synthesis was performed using the manufacturers' standard protocols.

The 5'-CPG support column, 5'-O-methyl-RNA phosphoramidites, 5'-O-methyl-dT-CE phosphoramidite, and sulfurizing reagent, 3H-1,2-benzodithiole-3-one-2,2-dioxide, were all obtained from Glen Research (Sterling, Va.).

To carry out a representative synthesis, the last seven bases of the desired sequence were entered into the 8909 Synthesizer, supplied with 2'-O-methyl-RNA phosphoramidites, the appropriate 5'-CPG column was attached, and a 1 µmole-scale RNA synthesis was performed with the final DMT on.

The column was then removed from the 8909 and attached to the ABI 394. The sulfurizing agent was installed in position 15 (to replace the oxidizer), and a synthesis for the phosphorothioate middle section of the oligo was carried out, using the 1 µmole Sulfur program with the final DMT on.

The column was then removed and replaced on the 8909. The last seven 2'-O-methyl RNA bases were added, using the 1 µmole RNA program, DMT on. Finally, the chain terminator, 5'-O-methyl-dT-CE (cyanoethyl) phosphoramidite, was added, using a 1 µmole DNA protocol modified to extend the coupling time to 300 seconds. The oligonucleotide was cleaved from the support, deprotected and gel purified using standard methods.

Example 2

Antisense Inhibition of Target RNA

A. Preparation of Transfection Mixture

For each transfection mixture, a carrier molecule, preferably a lipitoid or cholesteroid, was prepared to a working concentration of 0.5 mM in water, sonicated to yield a uniform solution, and filtered through a 0.45 µm PVDF membrane. The antisense oligonucleotide was prepared to a working concentration of 100 µM in sterile Millipore water.

The oligonucleotide was diluted in OptiMEM™ (Gibco/BRL), in a microfuge tube, to 2 µM, or approximately 20 µg oligo/ml of OptiMEM™. In a separate microfuge tube, lipitoid or cholesteroid, typically in the amount of about 1.5–2 nmol lipitoid/µg antisense oligonucleotide, was diluted into the same volume of OptiMEM™ used to dilute the oligonucleotide. The diluted antisense oligonucleotide was immediately added to the diluted lipitoid and mixed by pipetting up and down.

B. Transfection

Cells were plated on tissue culture dishes one day in advance of transfection, in growth media with serum, to yield a density at transfection of 60–90%. The oligonucleotide/lipitoid mixture was added to the cells, immediately after mixing, to a final concentration of 100–300 nM antisense oligonucleotide. Cells were incubated with the transfection mixture at 37° C., 5% $CO_2$ for 4–24 hours. After incubation, the transfection mixture was removed and replaced with normal growth media with serum.

Total RNA was extracted using the RNeasy™ kit (Quiagen Corporation, Chatsworth, Calif.), according to manufacturer's protocols.

C. Reverse Transcription

The level of target MRNA was quantitated using the Roche LightCycler™ real-time PCR machine. Values for the target MRNA were normalized versus an internal control (e.g. beta-actin).

For each 20 µl reaction, extracted RNA (generally 0.2–1 µg total) was placed into a sterile 0.5 or 1.5 µl microcentrifuge tube, and water was added to a total volume of 12.5 µl. To each tube was added 7.5 µl of a buffer/enzyme mixture, prepared by mixing (in the order listed) 2.5 µl $H_2O$, 2.0 µl 10X reaction buffer, 10 µl oligo dT (20 pmol), 1.0 µl dNTP mix (10 mM each), 0.5 µl RNAsin® (20u) (Ambion, Inc., Hialeah, Fla.), and 0.5 µl MMLV reverse transcriptase (50u) (Ambion, Inc.). The contents were mixed by pipetting up and down, and the reaction mixture was incubated at 42° C. for 1 hour. The contents of each tube were centrifuged prior to amplification.

D. LightCycler™ Amplification of RT Reactions

An amplification mixture was prepared by mixing in the following order: 1×PCR buffer II, 3 mM $MgCl_2$, 140 µM each dNTP, 0.175 pmol each oligo, 1:50,000 dil of SYBR® Green, 0.25 mg/ml BSA, 1 unit Taq polymerase, and $H_2O$ to 20 µl. (PCR buffer II is available in 10×concentration from Perkin-Elmer (Norwalk, Conn.). In 1×concentration it contains 10 mM Tris pH 8.3 and 50 mM KCl. SYBR® Green (Molecular Probes, Eugene, Oreg.) is a dye which fluoresces when bound to double Ad stranded DNA. As double stranded PCR product is produced during amplification, the fluorescence from SYBR® Green increases.).

To each 20 µl aliquot of amplification mixture, 2 µl of template RT was added, and amplification was carried out according to standard protocols.

Example 3

Cell Proliferation Assay

Cells were seeded into 96 well plates at a density of 5000 cells per well. For a 4 day proliferation assay, 5 independent 96 well plates were prepared, one for each day. After overnight incubation, cells were transfected using the procedure described above. On each day of the proliferation assay, all medium was removed from one plate and frozen at −70° C. On day four, all plates were developed with the Quantos™ assay kit (Stratagene, La Jolla, Calif.) which determines the amount of DNA, and thus the number of cells, in each well.

Example 4

Cytotoxicity Assay

Cells were seeded in 35 mm dishes at 35000 cells/well and allowed to attach overnight. Cells were then transfected with oligonucleotide/lipid formulations at 50–300 nM and incubated for 4 or 24 hours. Cells were harvested 12 hours later, including the medium containing floating cells. Live cells were then stained with propidium iodine (PI) to detect necrotic and apoptotic cells and counterstained with FITC-coupled Annexin V (which detects early and late apoptotic cells) according to the R&D Systems (Minneapolis, Minn.) Apoptosis Detection Kit instructions. The cells were then analyzed by FACS analysis to determine the relative number of PI+, annexin V+, PI+ annexin V+ and PI−/annexin V− cells. The results are expressed as percent (FIG. 8).

While the invention has been described with reference to specific methods and embodiments, it will be appreciated that various modifications may be made without departing from the invention.

It is claimed:

1. A composition comprising a chimeric oligonucleotide having the structure:

5'-W-X$^1$-Y-X$^2$-Z-3', wherein:
- W represents a 5'-O-alkyl nucleotide;
- each of X$^1$ and X$^2$ represents a block of seven to twelve phosphodiester-linked 2'-O-alkyl ribonucleotides;
- Y represents a block of five to twelve phosphorothioate-linked deoxyribonucleotides; and
- Z represents a blocking group effective to block nuclease activity at the 3' end of the oligonucleotide in a pharmaceutically acceptable vehicle.

2. The composition of claim 1, wherein the vehicle includes a lipid-cationic peptoid conjugate of the formula:

L-linker-[N(CH$_2$CH$_2$NH$_2$)CH$_2$(C=O)—
N(CH$_2$CH$_2$R)CH$_2$(C=O)—N(CH$_2$CH$_2$R)CH$_2$(C=O)]$_3$—NH$_2$ where
- L is selected from a lipid moiety comprising at least one fatty alkyl or alkenyl chain between about 8 and 24 carbon atoms in length and a steroid;
- each group R is independently selected from alkyl, aminoalkyl, and aralkyl, and
- the linker is selected from the group consisting of a direct bond, an oligopeptide, a substantially linear alkyl chain from 2 to about 30 bonds in length, and a substantially linear chain from 2 to about 30 bonds in length consisting of alkyl bonds and one or more linkages selected from the group consisting of ester, amide, carbonate, carbamate, disulfide, peptide, and ether.

3. The composition of claim 2, wherein the linker is from 3 to about 15 bonds in length.

4. The composition of claim 2, wherein said fatty alkyl or alkenyl chain is between about 14 and 24 carbon atoms in length.

5. The composition of claim 2, wherein L is a phospholipid group, having two fatty alkyl or alkenyl chains between about 8 and 24 carbon atoms in length.

6. The composition of claim 2, wherein L is a cholesteryl group.

7. The composition of claim 2, wherein R is isopropyl or 4-methoxyphenyl.

* * * * *

SEQUENCE LISTING

<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 1
ccatagtgag gttgcatctg gtgcc                                              25

<210> SEQ ID NO 2
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 2
gttcccttgc caaggagttt gagat                                              25

<210> SEQ ID NO 3
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 3
cccagagccg atggtccgat catgt                                              25

<210> SEQ ID NO 4
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 4
gacccacttc cctgaaaatc cgaaa                                              25

<210> SEQ ID NO 5
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 5
cggcgttttc ctttccctac aagc                                               24

<210> SEQ ID NO 6
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 6
agcggcagaa gttgaggtat gttga                                              25

<210> SEQ ID NO 7
<211> LENGTH: 25

```
<212> TYPE: DNA
<213> ORGANISM: Artificial Sequence
<220> FEATURE:
<223> OTHER INFORMATION: antisense oligonucleotide

<400> SEQUENCE: 7
cctgccagta tgaagttggg aagcg                                        25

<210> SEQ ID NO 8
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 8
gcgaagtccg tctgttcctg tttga                                        25

<210> SEQ ID NO 9
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 9
tcttcctcac agaccttcgg gcaag                                        25

<210> SEQ ID NO 10
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 10
tgctgatagt cgttgcggat gtcg                                         24

<210> SEQ ID NO 11
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 11
gtgtttgttc agggttccat ttcgg                                        25

<210> SEQ ID NO 12
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 12
gcatgtggaa ggtagggagg caaga                                        25

<210> SEQ ID NO 13
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 13
```

-continued accatatacc cagtgccttg tgcgg                                        25

<210> SEQ ID NO 14
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 14
gaagccccac ttgcggtcgt cat                                          23

<210> SEQ ID NO 15
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 15
acgagcaaag gcatcatcca ctgtc                                        25

<210> SEQ ID NO 16
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 16
gctttctctc ggtactggaa gacgt                                        25

<210> SEQ ID NO 17
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 17
aacccatgaa gttgcctgag cactg                                        25

<210> SEQ ID NO 18
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 18
tttcagggtg acgacctccc aagta                                        25

<210> SEQ ID NO 19
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 19
atctggtcgc ctcatttgct caact                                        25

<210> SEQ ID NO 20
<211> LENGTH: 25
<212> TYPE: DNA
<213> ORGANISM: Artificial Sequence

```
<220> FEATURE:
<223> OTHER INFORMATION: antisense oligonucleotide

<400> SEQUENCE: 20
tttcttcacg gttgcctact ggttc                                    25

<210> SEQ ID NO 21
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 21
tgatgaagag attcccatgc cgtcg                                    25

<210> SEQ ID NO 22
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 22
tgtagtcttt ccgaactgtg tgggc                                    25

<210> SEQ ID NO 23
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 23
ctgtgagcaa cagctgtcgt cgtct                                    25

<210> SEQ ID NO 24
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 24
ggcagtcatt agcagggtga tggtg                                    25

<210> SEQ ID NO 25
<211> LENGTH: 25
<212> TYPE: DNA
<213> ORGANISM: Artificial Sequence
<220> FEATURE:
<223> OTHER INFORMATION: reverse control of PDK1

<400> SEQUENCE: 25
tctgctgctg tcgacaacga gtgtc                                    25

<210> SEQ ID NO 26
<211> LENGTH: 25
<212> TYPE: DNA
<213> ORGANISM: Artificial Sequence
<220> FEATURE:
<223> OTHER INFORMATION: reverse control of AKT1

<400> SEQUENCE: 26
ccgtggtcta cgttggagtg atacc                                    25
```

```
<210> SEQ ID NO 27
<211> LENGTH: 25
<212> TYPE: DNA
<213> ORGANISM: Artificial Sequence
<220> FEATURE:
<223> OTHER INFORMATION: reverse control of AKT2

<400> SEQUENCE: 27
tagagtttga ggaaccgttc ccttg                                    25
```